United States Patent [19]
Willis

[11] Patent Number: 6,102,566
[45] Date of Patent: Aug. 15, 2000

[54] OSCILLATORY GUIDE FOR X-RAY CONE

[76] Inventor: Timothy G. Willis, 310 Evergreen, Yreka, Calif. 96097

[21] Appl. No.: 09/189,036

[22] Filed: Nov. 10, 1998

[51] Int. Cl.$^7$ ........................................................ A61B 6/14
[52] U.S. Cl. .......................... 378/170; 378/168; 378/169; 378/177
[58] Field of Search .................................... 378/168, 169, 378/170, 177

[56] References Cited

U.S. PATENT DOCUMENTS

| | | | |
|---|---|---|---|
| 4,598,416 | 7/1986 | Donato | 378/168 |
| 4,866,750 | 9/1989 | Chavarria et al. | 378/168 |
| 5,090,047 | 2/1992 | Angotti et al. | 378/170 |
| 5,256,982 | 10/1993 | Willis | 378/168 |
| 5,625,666 | 4/1997 | Willlis | 378/167 |
| 5,799,058 | 8/1998 | Willis et al. | 378/168 |

*Primary Examiner*—David V. Bruce
*Assistant Examiner*—Allen C. Ho
*Attorney, Agent, or Firm*—Flehr Hohbach Test Albritton & Herbert LLP

[57] ABSTRACT

A ring shaped to fit over the nose of a dental X-Ray machine cone locates the cone relative to selected teeth of the patent. The ring is mounted on an arm having a clip which fits over a hub to oscillate to different positions. The hub is a part of the handle for a locator for an X-Ray film packet or an X-Ray electronic sensor.

8 Claims, 3 Drawing Sheets

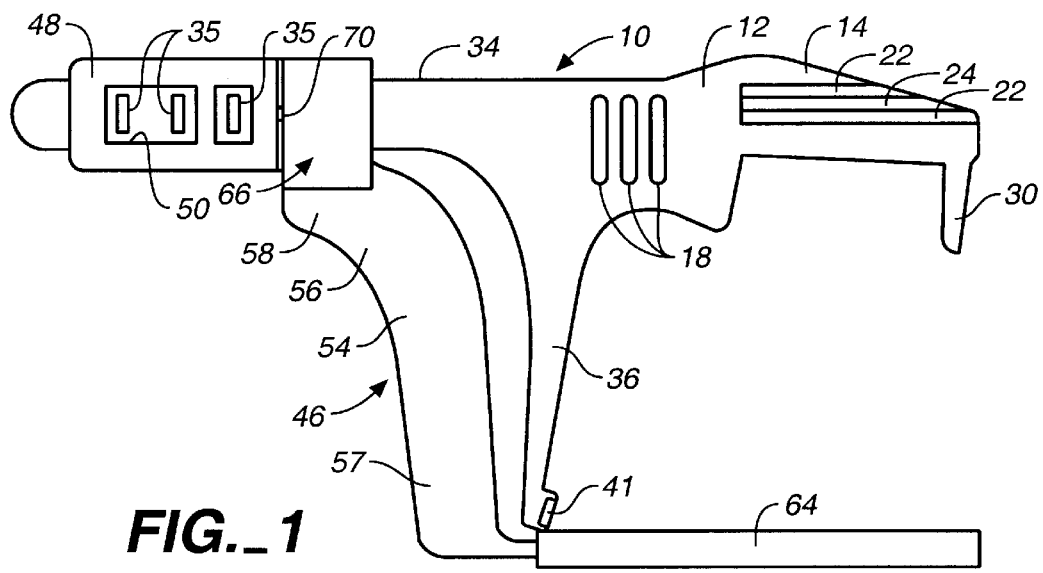
FIG._1
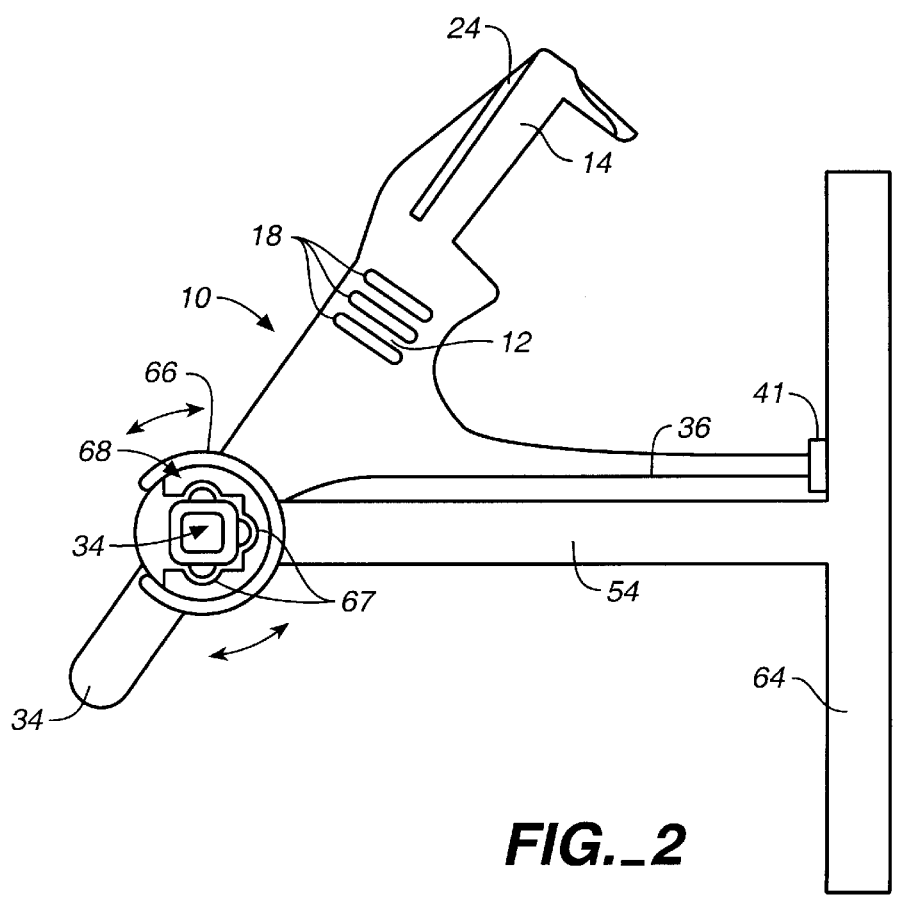
FIG._2

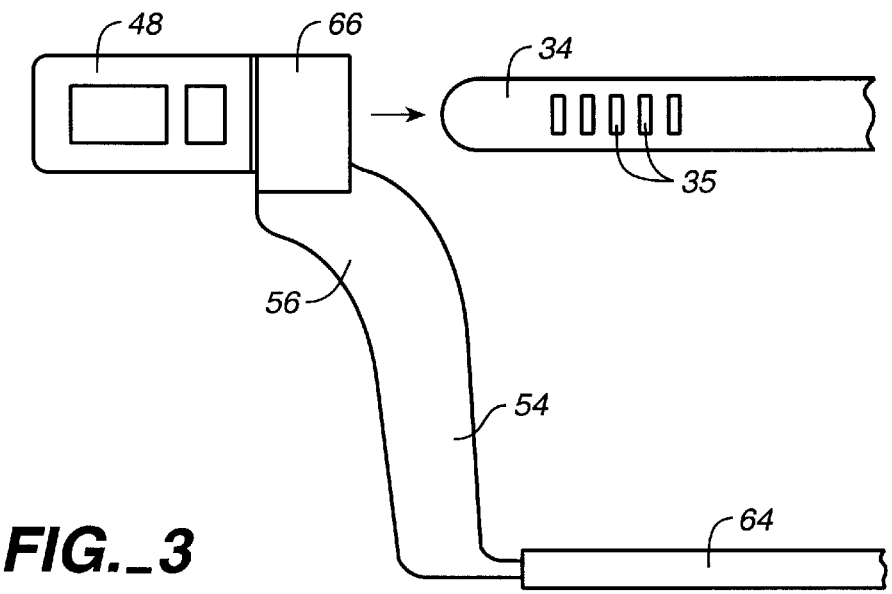
FIG._3
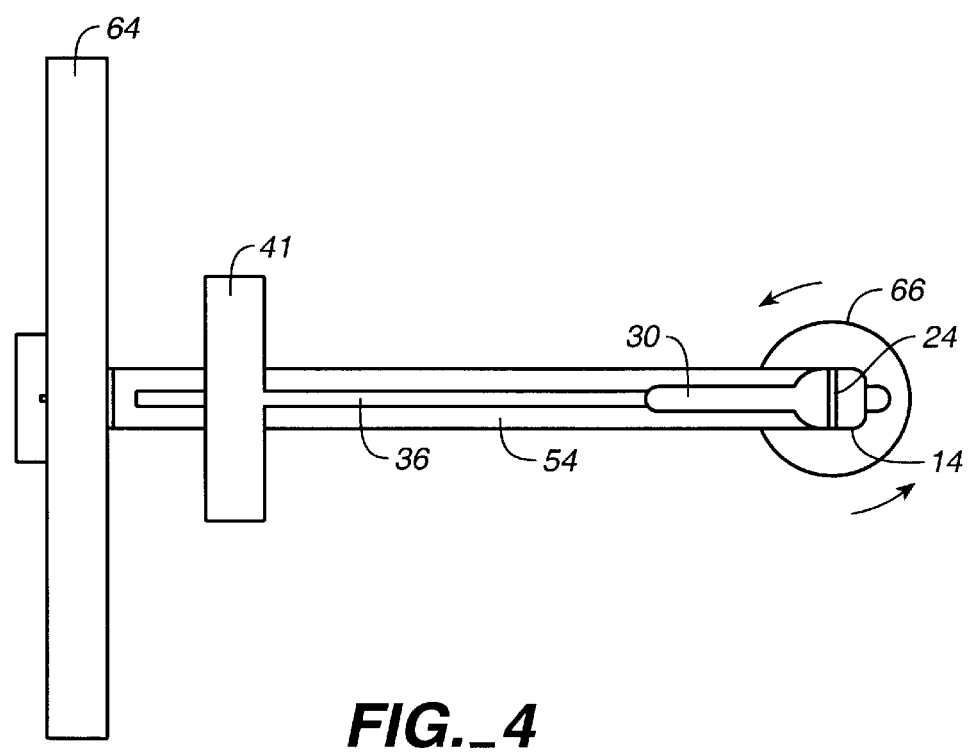
FIG._4

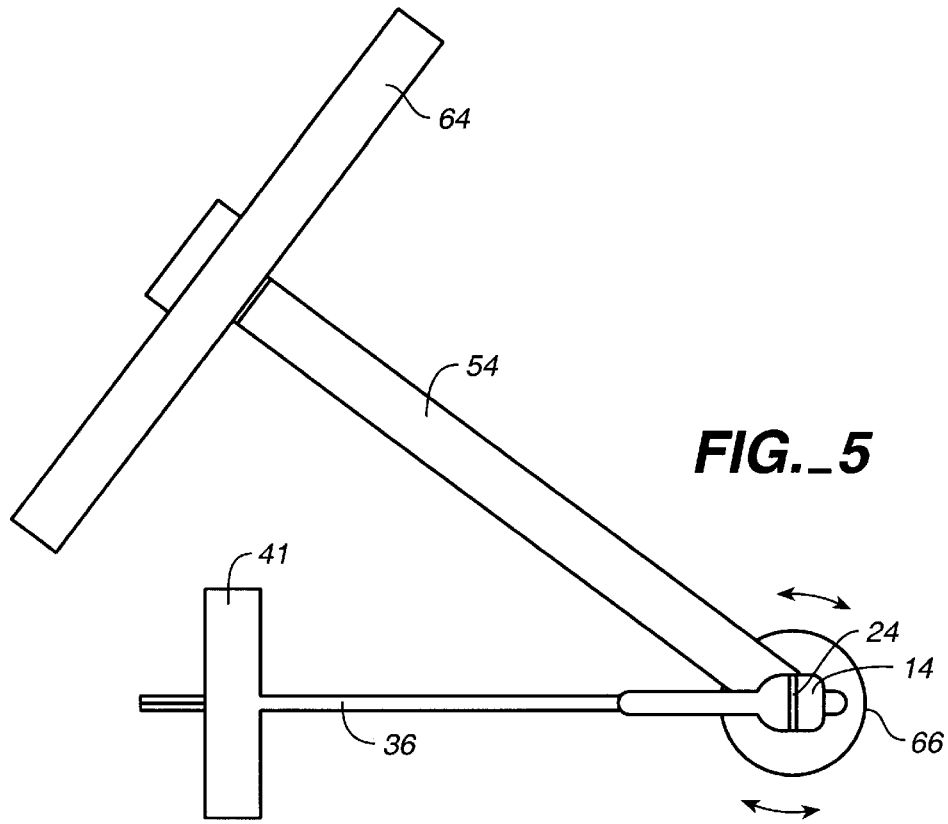
FIG._5
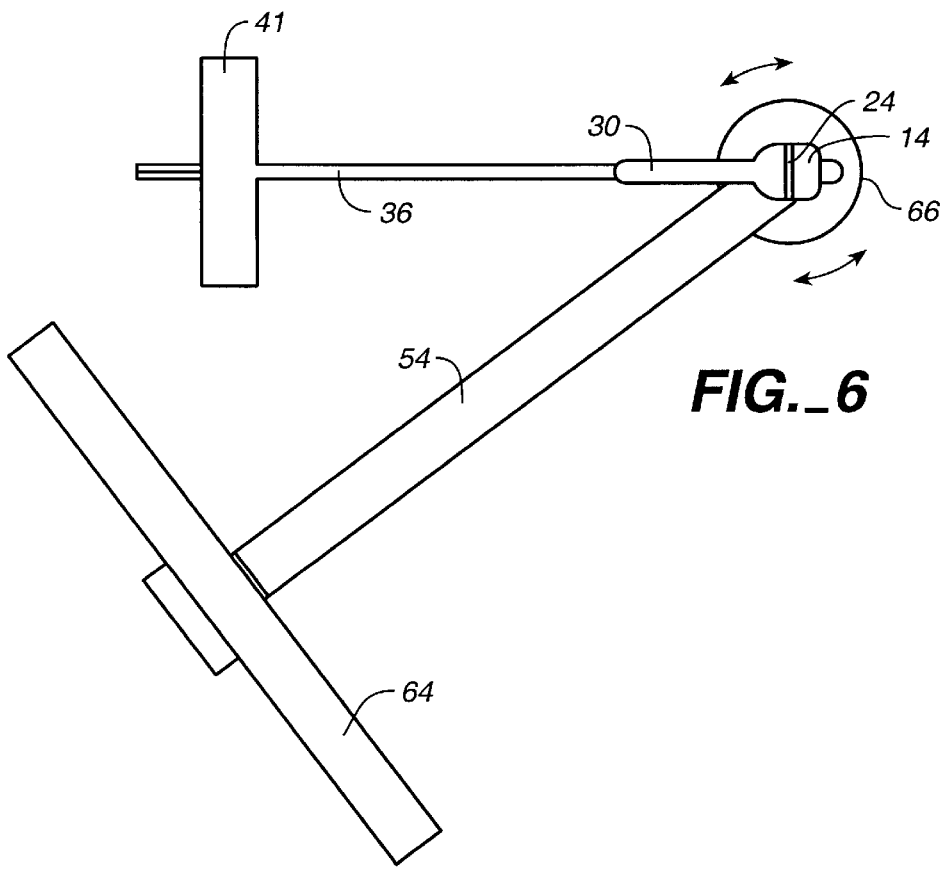
FIG._6

OSCILLATORY GUIDE FOR X-RAY CONE

BACKGROUND OF THE INVENTION

1. Field of the Invention.

This invention relates to a new and improved Oscillatory Guide for X-Ray Cone. More particularly the invention relates to a device held between the teeth of a patient to support an X-Ray film packet or an X-Ray electronic sensor together with a guide for the cone of the X-Ray machine.

2. Related Art

This invention comprises an improvement upon U.S. Pat. No. 5,799,058 which is, itself, an improvement upon U.S. Pat. Nos. 5,256,982 and 5,625,666.

SUMMARY OF THE INVENTION:

The invention comprises essentially two interfitting but detachable members. One member is a type of radiographic film holder or, alternatively, a device for retaining an electronic X-Ray sensor which holds a film packet or a sensor used to produce radiographic images of selected teeth of a patient's mouth. Such retaining device includes a thin bite portion which is shaped for placement between the upper and lower jaws. Distally of the bite portion is a grip for a film packet or a sensor. When the patient bites down on the bite portion, gripping it between his jaws, the retaining structure holds the packet or sensor lingually adjacent selected teeth. The retainer has a handle which extends out through the lips and is used by the technician for adjustment purposes.

A locator is formed with a ring shaped to fit around the exterior of a dental X-ray machine nose or cone to direct the X-Rays emitted therefrom toward the holder. The ring has an arm provided at its inner end with a swivel which fits over a hub on the handle in such manner that the ring may oscillate relative to the handle to position the ring in a variety of locations relative to the retainer. Further, because the handle is elongated, the distance between the cone and the packet or sensor may be adjusted, all while maintaining proper alignment of the emitted X-Rays in the plane of the film or sensor.

BRIEF DESCRIPTION OF THE DRAWINGS:

The accompanying drawings, which are incorporated in and form a part of this specification illustrate embodiments of the invention and, together with the description serve to explain the principles of the invention.

FIG. 1 is a top plan view showing the ring and retainer in assembled position.

FIG. 2 is an end elevation view as seen from the left of FIG. 1.

FIG. 3 is a fragmentary exploded view similar to FIG. 1.

FIGS. 4–6 are schematic views as viewed from the left of FIG. 1 showing the ring in three positions of adjustment.

DETAILED DESCRIPTION OF THE PREFERRED EMBODIMENT:

Reference will now be made in detail to the preferred embodiments of the invention, examples of which are illustrated in the accompanying drawings. While the invention will be described in conjunction with the preferred embodiments, it will be understood that they are not intended to limit the invention to those embodiments. On the contrary, the invention is intended to cover alternatives, modifications and equivalents, which may be included within the spirit and scope of the invention as defined by the appended claims.

Retainer 10 is similar to that shown in U.S. Pat. No. 5,799,058 and comprises a bite portion 12 which fits in the patient's mouth and has a distal retaining structure 14 to secure a film packet (not shown) or an electronic X-Ray sensor (not shown). A second bite portion 30 extends from bite portion 12 teeth alignment. Ridges 18 formed on bite portion 12 hold retainer in position when the patient bites thereon. Gripping members on the distal end 22 provide a slit 24 therebetween in to which a film packet (not shown) or a sensor may be inserted in various positions, depending upon the particular teeth to be X-Rayed. Extending outwardly is handle 34 which protrudes through the patient's lips and has transverse ridges 35 formed on the outer end thereof.

An arcuate locator 41 is disposed on the outer end of arm 36 as an alternate means to locate the cone of the X-Ray machines. Ring 64 may be substituted for the arcuate locator 41.

Locator 46 has a socket 48 which receives handle 34 in a slidable manner and is provided with an integral detent 50 which engages ridges 35 to secure the parts in desired positions of adjustment. Handle 34 may be moved longitudinally of socket 48 for such adjustment. Extending outwardly relative to socket 48 is an arm 54 having a curved portion 56 adjacent socket 48 and a distal portion 57 at right angles to handle 34. At the outer end of distal end 57 is a ring 64 dimensioned to receive the end of an X-Ray machine tip or cone. Distal end 58 is formed with a clip 66 which fits over a round cross-section swivel enlargement 68 on handle 34. The edge of clip 66 is formed with radial ridges 67. A single ridge 70 is formed on the end of handle 34 facing clip 66. Ridge 70 may seat in any of ridges 67 to detain arm 54 and hence, ring 64 in various positions of adjustment relative to handle 34 and thus, relative to the film held in slit 24. Thus, referring to FIGS. 4–6, the ring 64 may be positioned in at least three angular positions relative to film retaining structure 14. The teeth to be X-Rayed may be viewed directly horizontally toward the teeth as in FIG. 4, or from an angle above shown in FIG. 5 or from an angle below as shown in FIG. 6 depending upon the particular purpose of the X-Ray.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents.

What is claimed is:

1. A locator for the nose cone of a dental X-Ray machine for use with a holder for radiographic film or an electronic sensor said holder having a handle extending out of a patient's mouth comprising, a socket to receive a proximal end of said handle, a swivel on said socket, an arm projecting laterally of said swivel and having a distal end, a ring attached to said distal end of said arm, said ring being shaped to receive and align the cone to direct X-Rays emitted from said cone toward said holder, said swivel being oscillatory relative to said handle to direct X-Rays at a plurality of angles relative to said holder.

2. A locator according to claim 1 in which said arm is mounted oscillate relative to said handle.

3. A locator according to claim 1 in which said socket is movable along said handle in a plurality of positions of adjustment.

4. A locator according to claim 1 in which said handle is non-circular and said swivel turns relative to said handle.

5. In combination, a locator according to claim 2 and a retainer, said retainer comprising a bite portion configured for placement between a patient's jaws, a gripper for a film packet or a film sensor to hold a packet or sensor to lie lingually of and adjacent selected teeth, said handle extending from said bite portion out of the patient's mouth, said handle being dimensioned to fit into said socket.

6. The combination of claim 5 in which said handle is slidable relative to said socket.

7. The combination of claim 6 in which said socket is formed with a detent to detachably secure said handle relative to said locator.

8. The combination of claim 1 in which said ring has an axis and said arm is oscillatable relative to said holder to orient said ring axis between a first position perpendicular to said holder, a second position downwardly toward said holder and a third position upwardly toward said holder.

* * * * *

UNITED STATES PATENT AND TRADEMARK OFFICE
CERTIFICATE OF CORRECTION

PATENT NO : 6,102,566
DATED : August 15, 2000
INVENTOR(S) : WILLIS

It is certified that error appears in the above-identified patent and that said Letters Patent are hereby corrected as shown below:

IN THE CLAIMS:

Claim 2, Col. 3, line 2, after "mounted" insert --to--.

Signed and Sealed this

Seventeenth Day of April, 2001

Attest:

NICHOLAS P. GODICI

Attesting Officer

Acting Director of the United States Patent and Trademark Office